(12) United States Patent
Fortin et al.

(10) Patent No.: US 11,236,520 B2
(45) Date of Patent: Feb. 1, 2022

(54) CUSTOMIZABLE FACILITY

(71) Applicant: LONZA LTD, Visp (CH)

(72) Inventors: Jonathan Fortin, Hampstead, NH (US); Lesley Wood, Basel (CH); Stefan Widmer, Visp (CH); Sandra Carbonneau, Middleton, NH (US); Alexander Zahiri, Bad Krozingen (DE)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 15/455,836

(22) Filed: Mar. 10, 2017

(65) Prior Publication Data

US 2017/0260763 A1    Sep. 14, 2017

Related U.S. Application Data

(60) Provisional application No. 62/306,556, filed on Mar. 10, 2016.

(51) Int. Cl.
 *E04H 5/02* (2006.01)
 *E04H 1/00* (2006.01)
 (Continued)

(52) U.S. Cl.
 CPC ............ *E04H 1/005* (2013.01); *C12M 37/00* (2013.01); *E04H 5/00* (2013.01); *E04H 5/02* (2013.01);
 (Continued)

(58) Field of Classification Search
 CPC . E04H 1/005; E04H 5/00; E04H 5/02; C12M 37/00; F24F 3/161; E04B 2001/0053
 See application file for complete search history.

(56) References Cited

U.S. PATENT DOCUMENTS 4,667,580 A    5/1987    Wetzel
4,943,535 A *  7/1990    Thompson ............. C12M 29/08
                                                      435/295.3
(Continued)

FOREIGN PATENT DOCUMENTS

DE       9014558 A1    1/1991
DE       4218615 C1    7/1993
(Continued)

OTHER PUBLICATIONS

"GE Healthcare Life Sciences to Build KUBio Modular Biopharmaceutical Factory for JHL Biotech in China" BusinessWire.com (Sep. 25, 2013) Retrieved from http://www.businesswire.com/news/home/20130925005567/en/GE-Healthcare-Life-Sciences-Build-KUBio-Modular; Retrieved on Jun. 8, 2017.
(Continued)

*Primary Examiner* — Babajide A Demuren
(74) *Attorney, Agent, or Firm* — Medler Ferro Woodhouse & Mills PLLC

(57) ABSTRACT

A customizable facility for manufacturing at least one product has at least one modular unit in communication with at least one central unit configured to provide utilities to the at least one modular unit. In some embodiments, the central unit(s) and modular unit(s) are positioned at least partially within a shell. Each modular unit can be a fermentation unit, a pre-viral unit, a post-viral unit, a utility space, a warehouse, a media buffer facility, an office, a personnel unit, or another unit. The modular units can be arranged to maximize a number of modular units within the shell while minimizing a footprint of the shell. A method of assembling a facility for manufacturing at least one product includes providing at least one central unit and providing at least one modular unit in communication with the central unit(s) such that utilities are provided by the central unit(s) to the modular unit(s).

27 Claims, 11 Drawing Sheets

(51) Int. Cl.
*F24F 3/167* (2021.01)
*C12M 1/12* (2006.01)
*E04H 5/00* (2006.01)
*E04B 1/00* (2006.01)

(52) U.S. Cl.
CPC ...... *F24F 3/167* (2021.01); *E04B 2001/0053* (2013.01)

(56) References Cited

U.S. PATENT DOCUMENTS

| | | | |
|---|---|---|---|
| 5,272,071 A | 12/1993 | Chappel | |
| 5,474,411 A | 12/1995 | Schoenfeld et al. | |
| 5,633,162 A | 5/1997 | Keen et al. | |
| 5,656,491 A | 8/1997 | Cassani et al. | |
| 6,176,046 B1 | 1/2001 | Quine et al. | |
| 6,326,193 B1 | 12/2001 | Liu et al. | |
| 6,393,775 B1* | 5/2002 | Staschik | C02F 9/00 210/170.08 |
| 6,703,199 B1 | 3/2004 | Koide | |
| 7,182,858 B2 | 2/2007 | Brown et al. | |
| 7,629,167 B2 | 12/2009 | Davis et al. | |
| 8,298,054 B2 | 10/2012 | Hodge et al. | |
| 8,789,269 B2 | 7/2014 | Kilibarda et al. | |
| 9,158,345 B1* | 10/2015 | Rice | G06F 1/184 |
| 2001/0047628 A1* | 12/2001 | Mouton | E04B 1/3483 52/144 |
| 2002/0189173 A1* | 12/2002 | Staschik | C02F 9/00 52/79.1 |
| 2004/0079691 A1* | 4/2004 | Jowett | C02F 3/04 210/220 |
| 2005/0193643 A1* | 9/2005 | Pettus | B01L 99/00 52/79.1 |
| 2005/0235581 A1* | 10/2005 | Cohen | E04B 1/35 52/79.1 |
| 2009/0037031 A1 | 2/2009 | George et al. | |
| 2009/0300998 A1 | 12/2009 | Ablett | |
| 2009/0305626 A1 | 12/2009 | Hope | |
| 2010/0113294 A1 | 5/2010 | Venkataraman | |
| 2011/0053486 A1 | 3/2011 | Holtz et al. | |
| 2011/0240497 A1* | 10/2011 | Dechene | E04H 5/02 206/320 |
| 2011/0258837 A1* | 10/2011 | Scannon | G05B 19/4188 29/592 |
| 2012/0061869 A1 | 3/2012 | Boeckx et al. | |
| 2012/0077429 A1 | 3/2012 | Wernimont et al. | |
| 2013/0109291 A1* | 5/2013 | Holtz | B01L 1/04 454/187 |
| 2013/0164400 A1 | 6/2013 | Knopov et al. | |
| 2013/0233532 A1* | 9/2013 | Imwalle | F28F 27/02 165/287 |
| 2013/0280797 A1 | 10/2013 | Rao et al. | |
| 2013/0295672 A1 | 11/2013 | Planelles Carazo et al. | |
| 2015/0036266 A1* | 2/2015 | Emert | H05K 7/026 361/624 |
| 2015/0101264 A1* | 4/2015 | Jornitz | E04H 3/08 52/79.9 |
| 2015/0354201 A1* | 12/2015 | Gruetering | E04H 5/02 52/79.1 |
| 2016/0010883 A1* | 1/2016 | Jornitz | E03C 1/02 454/187 |
| 2016/0097074 A1 | 4/2016 | Collins et al. | |
| 2016/0105988 A1* | 4/2016 | Englert | H05K 7/1457 361/679.02 |
| 2016/0208209 A1* | 7/2016 | Thomas | C12M 37/00 |
| 2016/0312485 A1* | 10/2016 | Wilson | E04H 1/005 |
| 2016/0376784 A1* | 12/2016 | Timur | E04B 1/343 52/29 |
| 2017/0030097 A1* | 2/2017 | Marinoni | E04H 1/005 |
| 2017/0321443 A1* | 11/2017 | Biffiger | E04H 5/02 |

FOREIGN PATENT DOCUMENTS

| | | |
|---|---|---|
| DE | 102005036763 A1 | 2/2007 |
| EP | 2103548 A1 | 9/2009 |
| JP | H04368568 A | 12/1992 |
| JP | 2010524467 A | 7/2010 |
| JP | 2014503176 A | 2/2014 |
| WO | 0129058 A1 | 4/2001 |
| WO | 0196584 A2 | 12/2001 |
| WO | 2015117883 A1 | 8/2015 |

OTHER PUBLICATIONS

International Search Report and Written Opinion for International Application No. PCT/US2017/021838 dated Apr. 28, 2017.
International Search Report and Written Opinion for International Application No. PCT/US2017/043768 dated Nov. 13, 2017.
Fritchman et al. "Strategic Outsourcing of Media Design and Cell Culture Media Manufacturing" Biopharm International (2009) vol. 22, No. 9, pp. 18-19.
Haigney "Integrating Single-Use Systems in Pharma Manufacturing" Pharmatech (2016) vol. 40, No. 6, pp. 1-5 Retrieved from the Internet at http://www.pharmtech.com/inteoratina-single-use-systems-aharma-manufacturing Retrieved on Oct. 30, 2017.
International Search Report and Written Opinion for International Application No. PCT/US2017/045162 dated Nov. 17, 2017.
Shukla et al. "Single-use disposable technologies for biophramaceutical manufacturing" Trends in Biotechnology (2013) vol. 31, No. 3, pp. 147-154.

\* cited by examiner

CUSTOMIZABLE FACILITY

CROSS REFERENCE TO RELATED APPLICATIONS

This application claims the benefit of priority to U.S. Provisional Patent Application Ser. No. 62/306,556 filed on Mar. 10, 2016, which is hereby incorporated herein by reference in its entirety for all purposes.

FIELD OF THE INVENTION

The present disclosure relates to a customizable facility that enables a user to manufacture multiple products within the facility. In particular, the present disclosure relates to a customizable facility for manufacturing products in clean room settings.

BACKGROUND

Traditional structures for manufacturing products, such as monoclonal antibodies and microbial products, do not allow for efficient use of the space of the structure. The layout of traditional structures often limits them from being readily configured or expanded to manufacture a new product line. Thus, there is a need for a manufacturing facility that allows a user to efficiently use common resources between product lines and readily modify the facility to accommodate a new manufacturing process or a new manufacturing line with reduced facility down time.

SUMMARY

The present disclosure provides a customizable facility for manufacturing at least one product, utilizing at least one production process (e.g., a production process using a fermentation unit and a purification unit). According to one aspect of the present disclosure, the customizable facility includes a shell, at least one central unit positioned within the shell, and at least one modular unit, each modular unit being positioned within the shell. The shell, the central unit(s), and the modular unit(s) are configured and arranged to maximize the speed and ease of modifying manufacturing capacity of varying scope.

According to another aspect of the present disclosure, a customizable facility for manufacturing at least one pharmaceutical product, includes at least one central unit. At least one modular unit is in communication with the at least one central unit such that the at least one central unit provides utilities to the at least one modular unit.

In some embodiments, the customizable facility includes a shell, wherein the at least one central unit is positioned at least partially within the shell and the at least one modular unit is positioned at least partially within the shell.

In some embodiments, the at least one modular unit includes at least one of a fermentation unit, a pre-viral unit, a post-viral unit, a utility space, a warehouse, a media buffer facility, an office, a personnel unit, a production unit, a fill-finish unit, a dosage formulation unit, and a packaging unit.

In some embodiments, at least one of the at least one modular unit is directly adjacent to the at least one central unit.

In some embodiments, the at least one modular unit includes a plurality of modular units arranged to maximize a number of modular units within the shell while minimizing a footprint of the shell.

In some embodiments, each modular unit of the plurality of modular units is directly adjacent at least one of the at least one central unit and another one of the plurality of modular units.

In some embodiments, the at least one central unit and the plurality of modular units form a hub and spoke formation.

In some embodiments, the at least one central unit and the plurality of modular units are arranged in an H-shaped layout.

In some embodiments, the customizable facility includes a bioreactor supported on a ground surface within the shell.

In some embodiments, the customizable facility includes a bioreactor supported within one of the at least one modular unit.

In some embodiments, an outer wall of the customizable facility is one of: formed by the shell, the shell entirely enclosing the at least one central unit and the at least one modular unit; and formed by the shell and at least one of an outer wall of the at least one central unit and an outer wall of the at least one modular unit.

In some embodiments, the shell includes at least one side wall, the at least one side wall encircling the at least one central unit and the at least one modular unit, and a roof secured to an upper edge of the at least one side wall, the roof extending over the at least one central unit and the at least one modular unit.

In some embodiments, at least one of the at least one modular unit is a clean room.

In some embodiments, the at least one modular unit is configured for cell therapy operations.

According to another aspect of the present disclosure, a method of assembling a facility for manufacturing at least one pharmaceutical product includes providing at least one central unit; and providing at least one modular unit in communication with the at least one central unit such that the at least one central unit provides utilities to the at least one modular unit.

In some embodiments, the method includes providing a shell; positioning the at least one central unit at least partially within the shell; and positioning the at least one modular unit at least partially within the shell.

In some embodiments, the at least one modular unit includes at least one of a fermentation unit, a pre-viral unit, a post-viral unit, a utility space, a warehouse, a media buffer facility, an office, a personnel unit, a production unit, a fill-finish unit, a dosage formulation unit, and a packaging unit.

In some embodiments, the at least one modular unit includes a plurality of modular units arranged to maximize a number of modular units within the shell while minimizing a footprint of the shell.

In some embodiments, each modular unit of the plurality of modular units is directly adjacent at least one of the at least one central unit and another one of the at least one modular unit.

In some embodiments, the at least one central unit and the plurality of modular units form a hub and spoke formation.

In some embodiments, the at least one central unit and the plurality of modular units are arranged in an H-shaped layout.

In some embodiments, the method includes one of supporting a bioreactor on a ground surface within the shell and supporting a bioreactor within one of the at least one modular unit.

In some embodiments, an outer wall of the customizable facility is one of: formed by the shell, the shell entirely enclosing the at least one central unit and the at least one modular unit; and formed by the shell and at least one of an outer wall of the at least one central unit and an outer wall of the at least one modular unit.

In some embodiments, the shell includes at least one side wall, the at least one side wall encircling the at least one central unit and the at least one modular unit, and a roof secured to an upper edge of the at least one side wall, the roof extending over the at least one central unit and the at least one modular unit.

In some embodiments, the at least one pharmaceutical product is a biosimilar product.

DESCRIPTION OF THE FIGURES

The accompanying drawings are not intended to be drawn to scale. For purposes of clarity, not every component may be labeled in every drawing. In the drawings.

DETAILED DESCRIPTION

The structures disclosed herein for a customizable facility are useful for manufacturing at least one product at a given time. The structures disclosed herein are particularly useful for manufacturing a variety of products that utilize common resources.

The present disclosure provides systems and methods that allow for one or more scalable product lines to be at least partially enclosed within a shell of a customizable facility. Because the structure is adaptable, it does not require a user to commit the structure to a single product line for a long period of time. The structure can be reconfigured to meet the dimensional requirements of a product line.

The customizable facility of the present disclosure enables a user to decrease construction timelines, reduce capital expenditures, increase global design standardization, and to comply with various standards around the globe.

The customizable structure allows for shorter turnaround times from conception to construction, allows for decreased construction site congestion and requires fewer fixed assets when implementing a new product line.

Generally, the customizable facility comprises a shell, at least one central unit positioned within the shell, and at least one modular unit, each modular unit being positioned within the shell.

Figure 1:
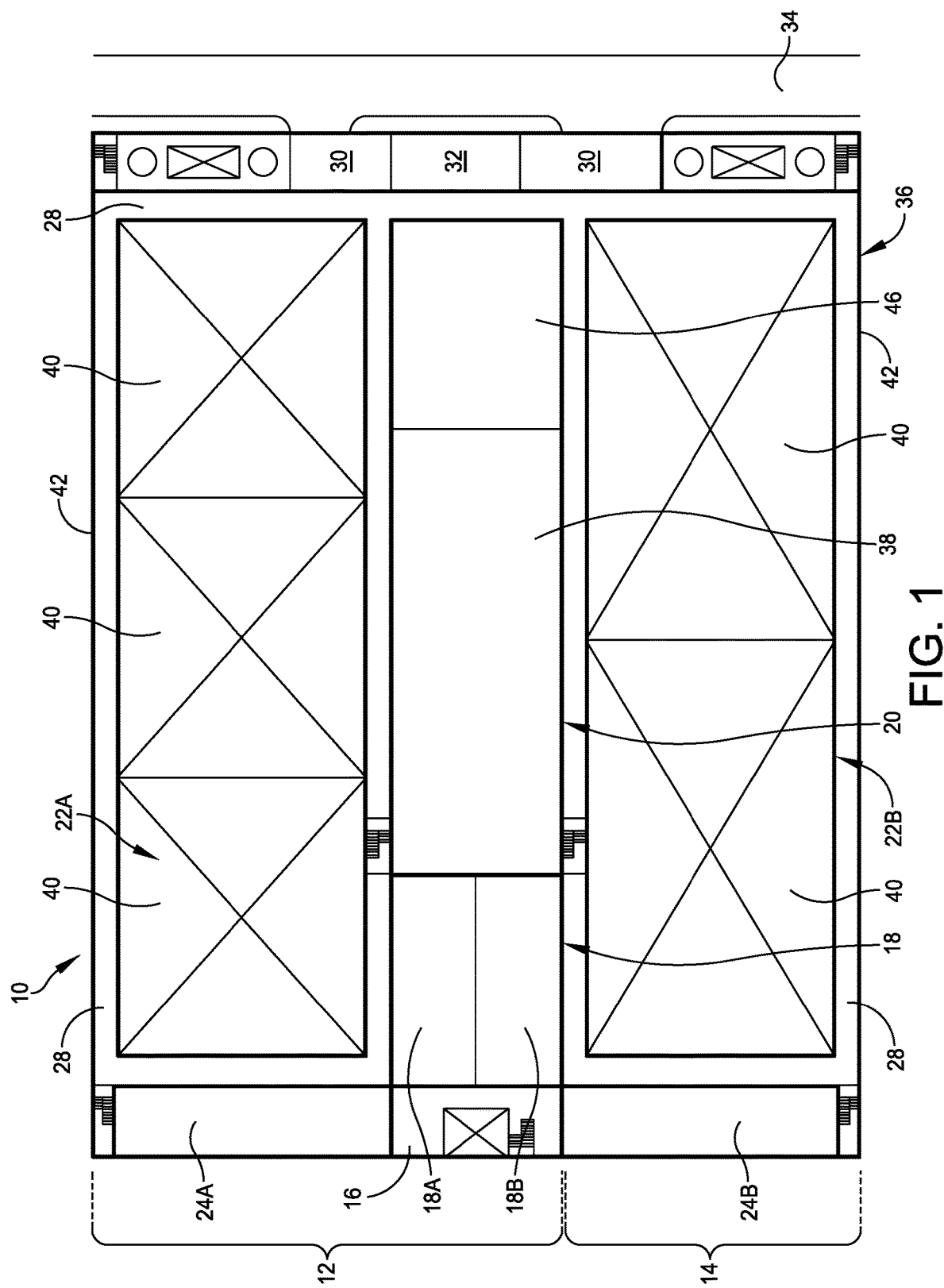
FIG. 1 is a top view of an embodiment of a customizable facility according to the present disclosure.

FIG. 1 is a top plan view of an exemplary embodiment of a customizable facility generally indicated at 10. The customizable facility of FIG. 1 can be constructed in a series of phases, such as a first phase 12, a second phase 14, and subsequent phases.

The features installed in the first phase 12 of construction of the customizable facility 10 of FIG. 1 include an air controlled entryway 16, a changing area 18, a utilities area 20, a first manufacturing wing 22A, a first office space 24A, and at least one corridor 28 allowing occupants of the customizable facility 10 to move within the customizable facility 10 from one area to another.

Outside of the customizable facility 10, there is a yard 30 that includes a handling area 32 for handling equipment and materials. The yard area 30 is shown adjacent to a roadway 34. Generally, the customizable facility 10 can be expanded in any direction. Additionally, the customizable facility 10 is constructed such that it can expand in a series of construction phases and/or sub-phases within the physical constraints of the surrounding features, such as the yard area 30 and the roadway 34.

FIG. 1 shows additional features that can be added during a second phase 14 of construction, such as a second manufacturing wing 22B and a second office 24B.

The layout of the customizable facility 10 can be configured for manufacturing in clean room settings. The customizable facility 10 utilizes a hybrid stick or frame build building and modular buildings with a utilities unit (or utility hub).

Referring now to FIGS. 2A-2E, the relative positions of various components of the customizable facility are shown.

Figure 2A:
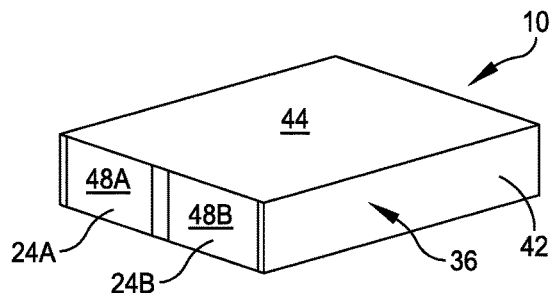
FIG. 2A is a perspective view of the embodiment of FIG. 1.

FIG. 2A shows a perspective view of the exterior walls of the outer shell 36 of the customizable facility 10. The outer shell (or shell) 36 at least partially encloses a central unit (which may be a central utilities unit) 38 and at least partially encloses a plurality of modular units 40, as discussed further below. In some embodiments, the outer shell 36 entirely encloses the utilities unit (which may be a central utilities unit) 38 and entirely encloses the plurality of modular units 40.

The outer shell 36 can be constructed according to traditional stick building or another method, such as, but not limited to, prefabricated modules. For example, the outer shell 36 can be fabricated from a steel structure using traditional building methods. The outer shell 36 can be supported on footings secured in the ground. The outer shell 36 is weatherproof.

The outer shell 36 forms a superstructure. In some embodiments, the outer shell 36 can be a "Butler" style building, which is known in the art of building construction.

The outer shell 36 includes side walls 42 that are dimensioned and configured to encircle one or more central units 38 and one or more modular units 40 included in the customizable facility 10, and described in more detail below.

A roof 44 is secured to upper edges of the side walls 42, with the roof 44 extending over the central unit(s) 38 and the modular unit(s) 40. Thus, the side walls 42 and the roof 44 enclose the central unit(s) 38 and the modular unit(s) 40, which are positioned within the shell 36. The central unit(s) 38 and the modular unit(s) 40 may be supported on a floor of the shell 36 or on another support surface on which the shell is secured. The customizable facility 10 provides a partially-modular (what could be called a modular stick build) method that includes a basic superstructure that is then filled in with modular type elements.

In one embodiment, the customizable facility 10 of FIG. 2A has an outer height of 30 meters. In one embodiment, each manufacturing wing has a length of 100 meters and a width of 30 meters.

Figure 2B:
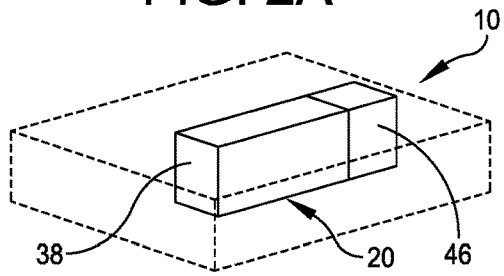
FIG. 2B is a perspective view of the embodiment of FIG. 1, showing a location of a component within the customizable facility.

FIG. 2B shows the exterior of the customizable facility 10 in broken lines, with the utilities area in solid lines. The utilities area 20 can include a central unit (which may be referred to as a Central Utility Bay (CUB) or utilities building or central utility module) 38 that is positioned towards the middle of the customizable facility 10.

The shell 36 of FIG. 1 also encloses a future utilities area 46, which is fully occupied by a future utilities module in FIG. 1. The future utilities area 46 is adjacent to the utilities module 38, and is shown in FIG. 1. The future utilities area 46 can be used as a warehouse area adjacent to the utilities module 38. The future utilities area 46 within this customizable facility 10 could also suite high bay applications, such as a 40 foot tall warehouse having an automated search and retrieval system (ASARS).

In some embodiments, the utilities module 38 and the future utilities area 46 are a single utilities module, which is divided into a utilities section and a future utilities section.

The central utility module 38 does not need to be at the center of the customizable facility 10. The central utility module 38 can be positioned along an outer edge of the customizable facility 10 in some embodiments.

Figure 2C:
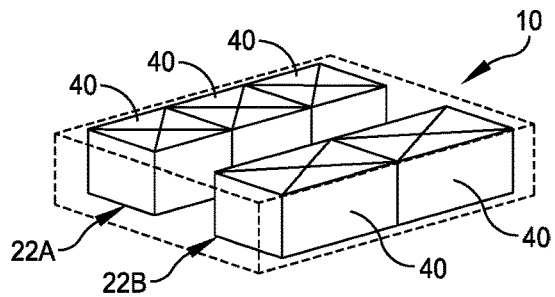
FIG. 2C is a perspective view of the embodiment of FIG. 1, showing a location of another component within the customizable facility.

FIG. 2C shows the exterior of the customizable facility 10 in broken lines, with the manufacturing wings 22A, 22B in solid lines.

The manufacturing wings 22A, 22B are configured to contain modular units 40 for a product line, such as fermentation modules or purification modules. The customizable facility 10 is easily expandable and scalable, and the different modular units 40 within the manufacturing wings 22A, 22B can be used to produce completely different products in the same customizable facility 10.

For example, in a modular unit 40 configured as a first fermentation module, a user could be manufacturing one type of product, such as a monoclonal antibody product derived from a mammalian cell line. In a second modular unit 40, the user could manufacture a completely different product, such as a microbial product. The customizable facility 10 of the present disclosure is capable of supporting multiple product lines simultaneously and multiple customers from a single, expandable superstructure. The customizable facility 10 of the present disclosure is capable of being expanded to add additional product lines.

Reactors can be supported within the modular units 40 of the manufacturing wings 22A, 22B of the customizable facility 10. The customizable facility 10 can support any desired and suitable vessel volume. For example, in some aspects such as that shown in FIG. 1, the customizable facility 10 can be configured to contain up to 20,000 liter production vessels, and storage vessels (e.g., harvest) in excess of 20,000 liters (e.g., 23,000-24,000 liters). For example, the customizable facility 10 can be dimensioned and configured to support vessels having a volume of about 20,000 liters, 15,000 liters, 10,000 liters, 5,000 liters, 2,000 liters and/or 1,000 liters. Vessels having other volumes can also be supported.

Any typical manufacturing and clean room equipment can be included in the customizable facility 10, and the customizable facility 10 can be fully suitable for cGMP (current good manufacturing practice) processes.

Examples of some equipment that can be fit in the customizable facility 10 include, but are not limited to: bioreactor, disc stack centrifuge, tangential flow filtration (TFF) skid, depth filtration skid, in-line dilution skid, chromatography columns with associated control equipment, media tank, harvest tank, purification vessels, depth filter holders, water softening and dechlorination system, clean steam generator, water for injection (WFI) storage tank, WFI break tank, WFI still, cooling towers, switchboard, emergency generator, chiller, hydronic pumps, autoclave, air handling units, process waste neutralization (such as a fiberglass reinforced plastic (FRP)), biowaste collection and inactivation system, clean-in-place systems, glass washer, and/or other equipment.

Bioreactors in the customizable facility 10 of the present disclosure can be ground based reactors. Alternatively, the bioreactors could be suspended from the structure itself. For example, the bioreactors could be suspended from one or more of the modular units 40.

The customizable facility 10 can include one or more central unit 38 and one or more modular unit 40. In some embodiments, each modular unit 40 is selected from the group of: a fermentation or cell culture unit, a pre-viral unit, a post-viral unit, a utility yard, a warehouse, a media buffer facility, an office, a personnel unit, a production unit, a fill-finish unit, a dosage formulation unit, and a packaging unit. A production unit is useful for manufacturing a product. A fill-finish unit is useful for filling a container such as a vial. A dosage formulation unit dispenses a set dose of a product. A packaging unit packages a product for distribution or sale.

The space allocated for each modular unit can be divided further as needed to fit specific processing requirements. Each manufacturing wing 22A, 22B can be configured to allow more than one modular unit 40 to be positioned within the respective manufacturing wing 22A, 22B.

In FIG. 1 and FIG. 2C, a first manufacturing wing 22A comprises three modular units 40. A second manufacturing wing 22B comprises two modular units 40. The central utilities area 20 has a length of 50 meters and a width of 20 meters, and has three internal levels. The central utilities block is expandable.

In some embodiments, at least one of the modular units 40 is a clean room. In some embodiments, at least one of the modular units 40 includes a clean room section within the respective modular unit 40.

The building shell 36 is designed to accommodate different production modules. In some embodiments, the shell can house four 20,000 liter vessels for a mammalian cell line. In some embodiments, the shell can house four 2,000 liter vessels for single-use technology operations.

In some embodiments, a manufacturing wing can include a modular unit containing four 20,000 liter vessels and downstream processing equipment and configured for manufacturing a monoclonal antibody product derived from a mammalian cell line, a modular unit containing single-use equipment for manufacturing a monoclonal antibody product derived from a mammalian cell line having four 20,000 liter vessels, a modular unit configured for manufacturing a microbial product, and/or a modular unit containing single-use equipment for manufacturing a microbial product.

In one embodiment, a modular unit is configured for mammalian manufacturing and includes four 20,000 liter vessels and downstream processing equipment. In another embodiment, a modular unit includes four 20,000 liter vessels for commercial and clinical production. In another embodiment, a modular unit includes one 1,000 liter vessel for clinical production. In another embodiment, a modular unit is configured for manufacturing a microbial product, and includes one 15,000 liter vessel. In another embodiment, a modular unit includes three 5,000 liter vessels. In another embodiment, a modular unit includes one or more process development labs. In another embodiment, a modular unit includes fill and finish clinical development vial fill equipment, one or more set of lyophilizing equipment, equipment for manufacturing pre-filled syringes, and/or equipment for manufacturing high potency products for commercial applications. In some embodiments, a modular unit includes cell therapy equipment. In some embodiments, a modular unit includes viral therapy equipment.

Figure 2D:
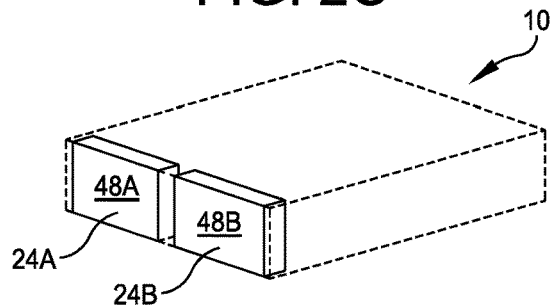
FIG. 2D is a perspective view of the embodiment of FIG. 1, showing a location of another component within the customizable facility.

FIG. 2D shows the exterior of the customizable facility 10 in broken lines, with the first office space 24A and the second office space 24B in solid lines. The first office space 24A includes offices, lockers for personal storage, and a support area. The second office space 24B includes offices, lockers for personal storage, and a support area. The front wall 48A of the first office space 24A forms a portion of the front outer surface of the customizable facility 10, as shown in FIG. 2A. The front wall 48B of the first office space 24B forms a portion of the front outer surface of the customizable facility 10. Thus, each office space 24A, 24B is only partially enclosed by the shell 36 of the customizable facility 10.

Similarly, in some embodiments, an outer wall of the central unit and/or an outer wall of one of the at least one modular units forms at least a part of the outer wall of the customizable facility. In some embodiments, an upper surface of a central utility module and/or an upper surface of a modular unit forms part of an upper surface of the customizable facility.

Figure 2E:
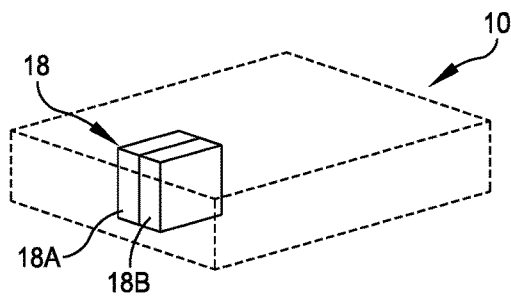
FIG. 2E is a perspective view of the embodiment of FIG. 1, showing a location of another component within the customizable facility.

FIG. 2E shows the exterior of the customizable facility 10 in broken lines, with the changing area 18 in solid lines. The changing area 18 allows users to enter the customizable facility 10 and change from street clothes into work clothes. The changing area 18 in FIG. 2E is further subdivided into a male changing area 18A and a female changing area 18B. In some embodiments, the changing area 18 is subdivided into two or more changing areas. In some embodiments, the changing area 18 is not subdivided.

In other embodiments, the relative positions of the first manufacturing wing 22A and second manufacturing wings 22B, the first office space 24A, the second office space 24B, the changing area 18, and the utilities area 20 can be positioned differently in the customizable facility 10 and/or oriented differently with respect to the customizable facility 10.

Scaffolding and corridors 28 allow users of the customizable facility 10 to access the utilities unit 38 of the utilities area 20 and the modular units (fermentation, etc. modules) 40.

After adding the second phase 14 of construction to the customizable facility 10, over time a user may wish to further expand the customizable facility 10. For example, consumers in the global economy may develop increased demand for a product that the user is manufacturing, or consumers in the global economy may develop increased demand for a product that the user could produce. To respond to such increases in demand for a product, the user can expand the customizable facility 10 in subsequent phases of construction that add additional features to the customizable facility of FIG. 1. In some embodiments, such additional features (such as additional modular units, an additional manufacturing wing, or another component of a customizable facility) are positioned horizontally adjacent to the first manufacturing wing 22A or the second manufacturing wing 22B. In some embodiments, such additional features are positioned vertically adjacent to the first manufacturing wing 22A and/or the second manufacturing wing 22B.

Referring now to FIGS. 3A-3E, it is possible for a user to expand a manufacturing wing, such as the first manufacturing wing 22A or the second manufacturing wing 22B of FIG. 1, in different sub-phases. A user could convert a manufacturing wing layout from one of the configurations shown in FIGS. 3A-3E to another configuration shown in FIGS. 3A-3E. Alternatively, a user could convert a manufacturing wing layout to another configuration.

Figure 3E:
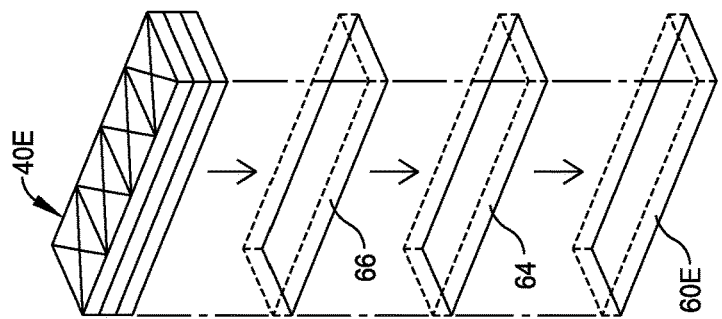
FIG. 3E is an exploded view of another embodiment of a modular unit according to the present disclosure.
Figure 3D:
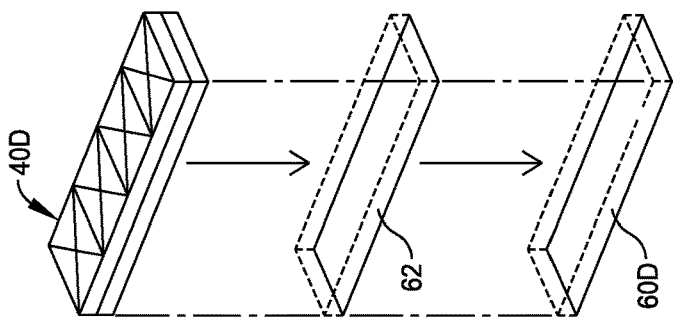
FIG. 3D is an exploded view of another embodiment of a modular unit according to the present disclosure.
Figure 3C:
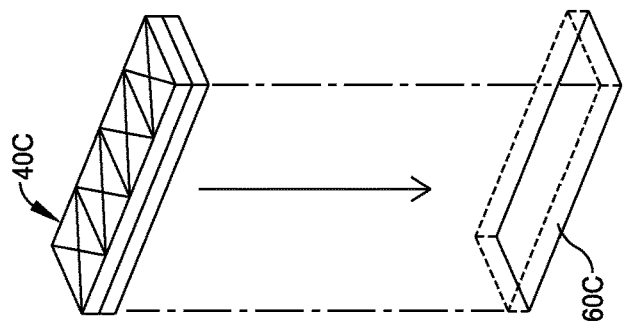
FIG. 3C is an exploded view of another embodiment of a modular unit according to the present disclosure.
Figure 3B:
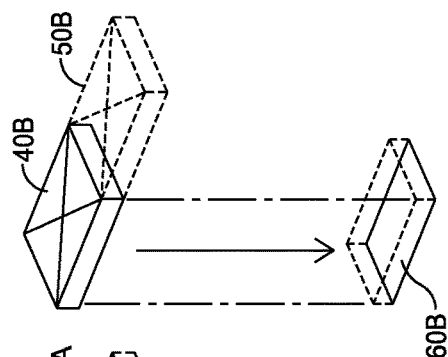
FIG. 3B is an exploded view of another embodiment of a modular unit according to the present disclosure.
Figure 3A:
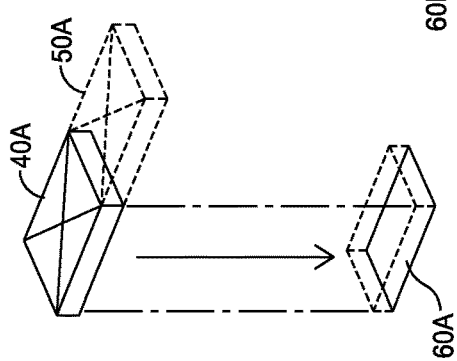
FIG. 3A is an exploded view of an embodiment of a modular unit according to the present disclosure.

FIG. 3A shows a partially exploded view of an embodiment of a modular unit 40A that is configured as a fill finish module. The fill finish module of FIG. 3A has a single floor 60A with a footprint of 1,500 square meters. The fill finish module includes a mezzanine for an HVAC plant room and some localized utilities. A free field 50A is shown in broken lines adjacent to the fill finish module, and has a footprint of 1,500 square meters. The free field 50A can be used for a variety of purposes, such as product storage. Together, the fill finish module 40A and the free field 50A extend over the 3,000 square meter footprint of the second manufacturing wing 22B.

FIG. 3B shows a partially exploded view of an embodiment of a modular unit 40B that is configured as a "2 k module." The 2 k module of FIG. 3B has a single floor 60B with a footprint of 1,500 square meters. The 2 k module can enclose a 2,000 liter vessel. The 2 k module includes a mezzanine for an HVAC plant room and some localized utilities. A free field 50B is shown in broken lines adjacent to the 2 k module, and has a footprint of 1,500 square meters. The free field 50B can be used for a variety of purposes, such as product storage. Together, the 2 k module 40B and the free field 50B extend over the 3,000 square meter footprint of the second manufacturing wing 22B.

FIG. 3C shows a partially exploded view of an embodiment of a modular unit 40C that is configured as "a 5 k module." The 5 k module of FIG. 3C has a single floor 60C with a footprint of 3,000 square meters. The 5 k module can enclose a 5,000 liter vessel. The 5 k module includes a mezzanine for an HVAC plant room and some localized utilities. The 5 k module extends over the 3,000 square meter footprint of the manufacturing wing.

FIG. 3D shows a partially exploded view of an embodiment of a modular unit 40D that is configured as a "15 k module." The 15 k module of FIG. 3D has a first floor 60D and a second floor 62. The 15 k module of FIG. 3D has a footprint of 3,000 square meters. The 15 k module can enclose a 15,000 liter vessel. The 15 k module includes a local HVAC unit, a clean in place (CIP) unit, and a temperature control unit (TCU). The temperature control unit in some embodiments includes water jackets with heat exchangers on a tank to control the temperature of a tank used in a product line. A CIP unit is typically a modular skid and has several tanks to hold a cleaning solution (such as caustic solutions and bleach), pumps, and sensors to send the cleaning solution to the appropriate tank to be cleaned.

The first floor 60D of the 15 k module extends over the 3,000 square meter footprint of the manufacturing wing. The second floor 62 of the 15 k module extends vertically above the first floor of the 15 k module, and extends above the 3,000 square meter footprint of the manufacturing wing. Together, the first floor 60D of the 15 k module and the second floor 62 of the 15 k module have a combined area of 6,000 square meters.

FIG. 3E shows a partially exploded view of an embodiment of a modular unit 40E that is configured as a "20 k module." The 20 k module of FIG. 3E has a footprint of 3,000 square meters. The 20 k module can enclose a 20,000 liter vessel. The 20 k module includes a local HVAC unit, a CIP unit, and a TCU. The 20 k module includes a first floor, a second floor, and a third floor. The first floor 60E of the 20 k module extends over the 3,000 square meter footprint of the manufacturing wing. The second floor 64 of the 20 k module extends vertically above the first floor 60E of the 20 k module, and extends above the 3,000 square meter footprint of the manufacturing wing. The third floor 66 of the 20 k module extends vertically above the first floor 60E of the 20 k module and the second floor 64 of the 20 k module, and extends above the 3,000 square meter footprint of the manufacturing wing. Together, the first floor 60E of the 20 k module, the second floor 64 of the 20 k module, and the third floor 66 of the 20 k module have a combined area of 9,000 square meters.

Figure 4:
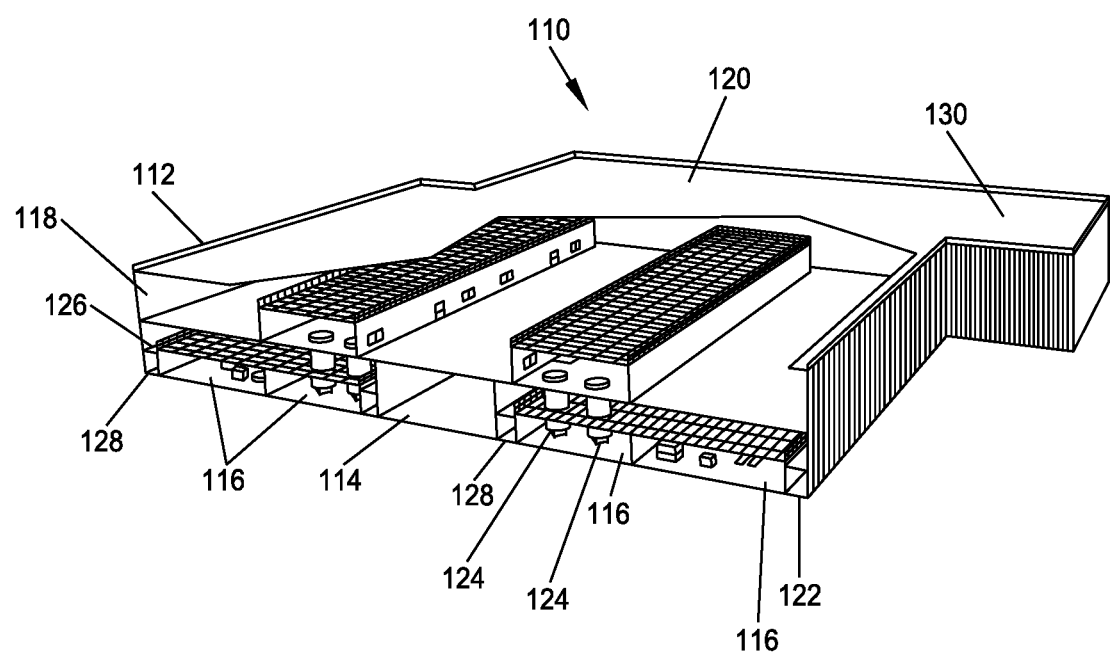
FIG. 4 is a front perspective cutaway view of an embodiment of a customizable facility according to the present disclosure.

FIG. 4 is a front perspective cutaway view of an exemplary embodiment of a customizable facility generally indicated at 110 according to the present disclosure. The customizable facility 110 layout can be configured for manufacturing in clean room settings. The customizable facility 110 utilizes a hybrid stick or frame build building and modular buildings with a centrally located utility hub (or central unit) 114.

An outer shell (or shell) 112 encloses a central unit 114 and a plurality of modular units 116 adjacent to the central unit 114. The outer shell 112 can be constructed according to traditional stick building or another method, such as, but not limited to, prefabricated modules. For example, the outer shell 112 can be fabricated from a steel structure using traditional building methods. The outer shell 112 can be supported on footings secured in the ground. The outer shell 112 is weatherproof.

The outer shell 112 forms a superstructure. In some embodiments, the outer shell 112 can be a "Butler" style building, which is known in the art of building construction.

The shell 112 includes side walls 118 that are dimensioned and configured to encircle one or more central units 114 and one or more modular units 116 included in the customizable facility 110, and described in more detail below. A roof 120 is secured to upper edges of the side walls 118, with the roof 120 extending over the central unit(s) 114 and the modular unit(s) 116. Thus, the side walls 118 and the roof 120 enclose the central unit(s) 114 and the modular unit(s) 116, which are positioned within the shell 112. The central unit(s) 114 and the modular unit(s) 116 may be supported on a floor 122 of the shell 112 or on another support surface on which the shell 112 is secured. The customizable facility 110 provides a partially-modular (what could be called a modular stick build) method that includes a basic superstructure that is then filled in with modular type elements.

Within the shell 112, the customizable facility 110 of FIG. 4 includes at least one central unit 114, which each may be referred to as a Central Utility Bay (CUB). The central unit 114 provides central utilities in FIG. 4. As shown, the CUB 114 is in the middle of the structure with modular units 116, which may be referred to as manufacturing pods, which stem from the CUB 114 (or from a plurality of CUBs). In FIG. 4, the modular units 116 are fermentation modules. The customizable facility 110 is easily expandable and scalable, and the pod/modular approach (i.e., a hub and spoke type approach) allows the different modules to produce completely different products in the same customizable facility 110.

For example, in a first fermentation module, such as the fermentation module on the left of FIG. 4, a user could be manufacturing one type of product, such as a monoclonal antibody product derived from a mammalian cell line. In a second module, such as the fermentation module on the right of FIG. 4, the user could manufacture a completely different product, such as a microbial product. The customizable facility 110 of the present disclosure is capable of supporting multiple product lines simultaneously and multiple customers from a single, expandable superstructure.

FIG. 4 shows reactors 124 supported within the customizable facility 110. The customizable facility 110 can support any desired and suitable vessel volume. For example, in some aspects such as that shown in FIG. 4, the facility 110 can be configured to contain up to 20,000 Liter production vessels, and storage vessels (e.g., harvest) in excess of 20,000 liters (e.g., 23,000-24,000 liters). For example, the customizable facility 110 can be dimensioned and configured to support vessels 124 having a volume of about 20,000 liters, 15,000 liters, 10,000 liters, 5,000 liters, 2,000 liters and/or 1,000 liters. Vessels 124 having other volumes can also be supported.

Scaffolding 126 and corridors 128 allow users of the facility 110 to access the central unit (central utility) 114 and the modular units (fermentation, etc. modules) 116. As shown in FIG. 4, the scaffolding 126 is positioned within the shell 112.

In some embodiments, one or more central units (CUBs) 114 and the one or more modular units 116 are arranged in a hub and spoke arrangement.

Any typical manufacturing and clean room equipment can be included in the customizable facility 110, and the customizable facility 110 can be fully suitable for cGMP processes.

Examples of some equipment that can be fit in the facility 110 include, but are not limited to: bioreactor, disc stack centrifuge, tangential flow filtration (TFF) skid, depth filtration skid, in-line dilution skid, chromatography columns with associated control equipment, media tank, harvest tank, purification vessels, depth filter holders, water softening and dechlorination system, clean steam generator, water for injection (WFI) storage tank, WFI break tank, WFI still, cooling towers, switchboard, emergency generator, chiller, hydronic pumps, autoclave, air handling units, process waste neutralization (such as a fiberglass reinforced plastic (FRP)), biowaste collection and inactivation system, clean-in-place systems, glass washer, and/or other equipment.

Bioreactors in the customizable facility 110 of the present disclosure can have ground based reactors 124 as is shown in FIG. 4. Alternatively, the bioreactors 124 could be suspended from the structure itself. For example, the bioreactors 124 could be suspended from one or more of the modular units 116.

The shell 112 of FIG. 4 encloses a warehouse area 130 towards the back right of the facility 110. The warehouse area 130 within this facility 110 could also suite high bay applications, such as a 40 foot tall warehouse having an automated search and retrieval system (ASARS).

The customizable facility 110 can include one or more central unit 114 and one or more modular unit 116. In some embodiments, each modular unit 116 is selected from the group of: a fermentation or cell culture unit, a pre-viral unit, a post-viral unit, a utility yard, a warehouse, a media buffer facility, an office, a personnel unit, a production unit, a fill-finish unit, a dosage formulation unit, and a packaging unit. The space allocated for each modular unit can be divided further as needed to fit specific processing requirements.

In some embodiments, at least one of the modular unit(s) 116 is a clean room.

Figure 5:
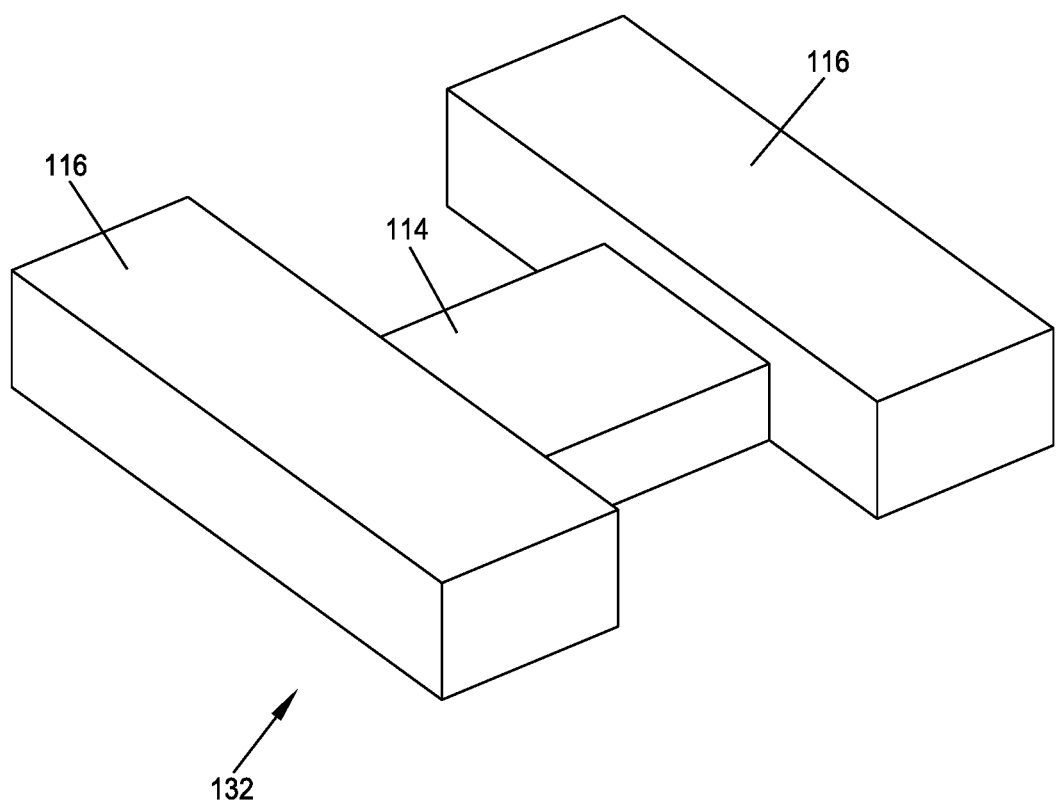
FIG. 5 is a perspective view of a set of modular units and a central unit arranged in an H-shaped layout.

FIG. 5 shows a perspective view of a set of a central unit 114 and modular units 116 arranged in an H-shaped layout 132. The position of each modular unit 116 can be adjusted to best fit processing requirements.

Figure 6:
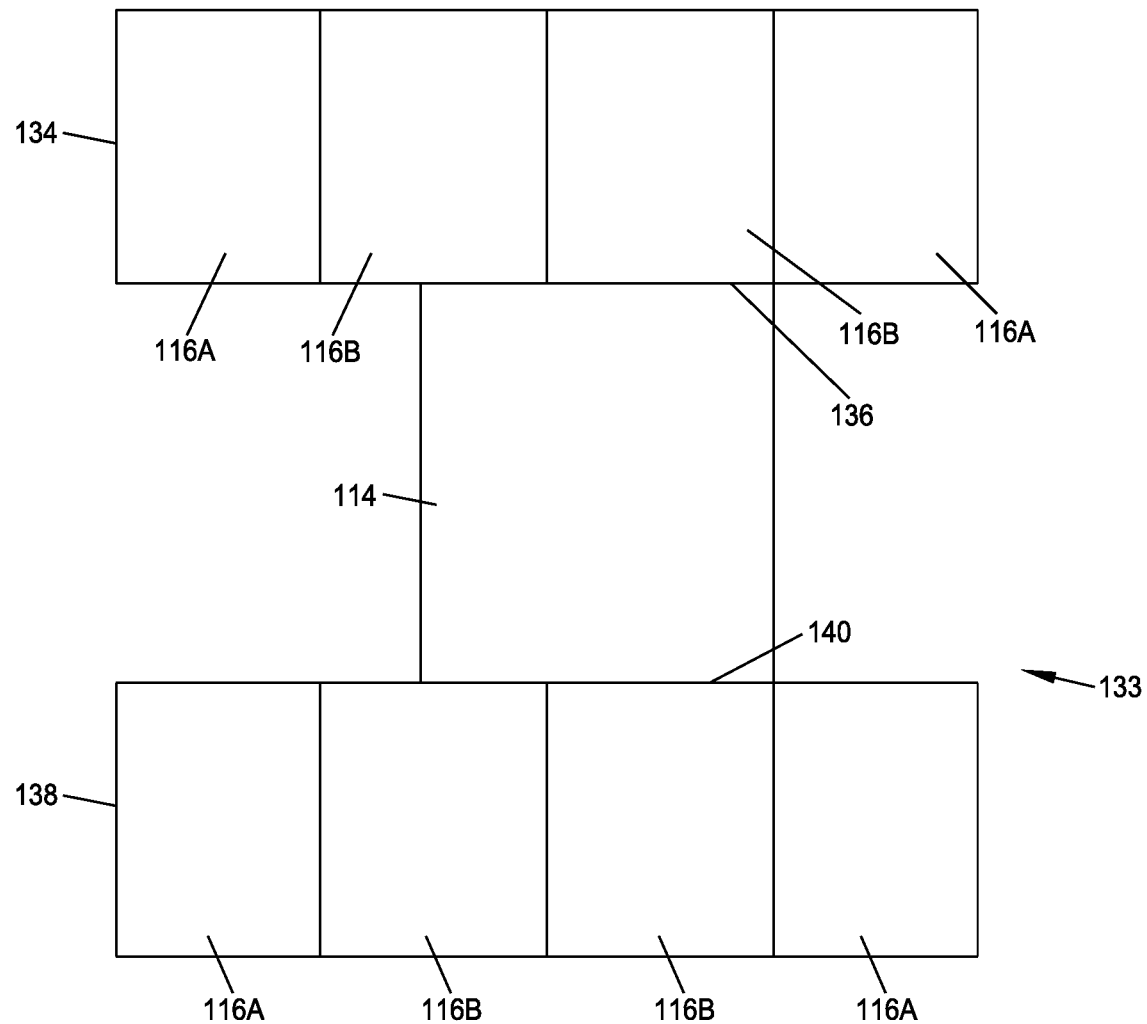
FIG. 6 is a top view of a set of modular units and a central unit arranged in an H-shaped layout.
Figure 7:
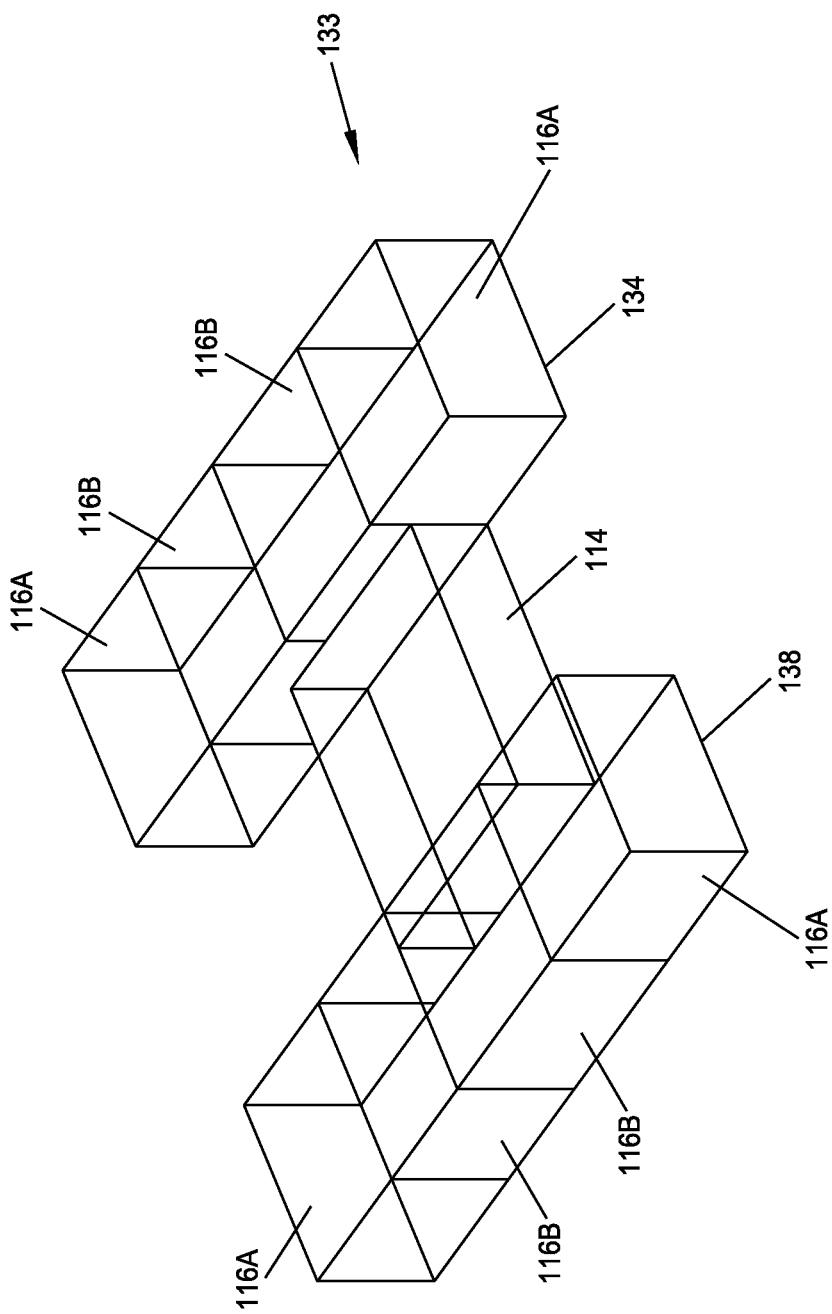
FIG. 7 is a perspective view thereof.

FIGS. 6 and 7 show an embodiment of a customizable facility in which a central unit 114 and a set of eight modular units, configured as purification units 116A and fermentation units 116B, are arranged in an H-shaped layout 133 when viewed from above. The shell 112 is not shown in these views. The plan view of FIG. 6 shows a central unit (labeled as a central utilities building) 114 having a first row of modular units, configured as purification units 116A and fermentation units 116B, arranged in a linear array 134 adjacent to a first side 136 of the central unit 114, and a second row of modular units, configured as purification units 116A and fermentation units 116B, arranged in a linear array 138 adjacent to a second side 140 of the central unit 114. The array 134 of modular units includes four modular units, with a first purification unit 116A at a first end of the array 134, two fermentation units 116B at the middle of the array 134, and a second purification unit 116A at a second end of the array 134. Similarly, the array 138 of modular units includes four modular units, with a first purification unit 116A at a first end of the array 138, two fermentation units 116B at the middle of the array 138, and a second purification unit 116A at a second end of the array 138.

The two fermentation units 116B of the first array 134 of modular units each include a side wall that is in direct facing engagement with a first side wall 136 of the central unit 114. Similarly, the two fermentation units 116B of the second array 138 of modular units each include a side wall that is in direct facing engagement with a second side wall 140 of the central unit 114. The purification units 116A are in direct facing relation with their respectively adjacent fermentation units 116B. Because of the direct facing engagement of the central unit 114 and the fermentation units 116B, the number of central units 114 and modular units that can fit within a shell 112 of a given size is increased. Likewise, the footprint of a shell 112 required to enclose a given set of central units 114 and modular units is decreased. Optionally, in some aspects the side walls of the fermentation units 116B (or other modular units) need not be in direct facing engagement but could be spaced so as to provide any desired footprint.

The modular unit(s) 116 and the central unit(s) 114 can be arranged to facilitate manufacture of a plurality of products simultaneously. The modular unit(s) 116 and central unit(s) 114 are arranged to efficiently share resources between the manufacturing lines of the respective products. For example, in some embodiments, the central unit 114 contains at least one of: a power generator, plumbing lines, power lines, and other resources that can be shared by the modular units 116. Additionally, the modular unit(s) 116 and the central unit(s) 114 can be arranged to facilitate future expansion of manufacturing capacity. For example, a single modular unit 116 can be utilized initially, with ability to add additional modular units 116 at a later time with minimal impact to existing operations.

In some embodiments, each of the modular units 116 includes its own respective heating, ventilation, and air conditioning (HVAC) system, as required for operation and segregation.

Figure 10:
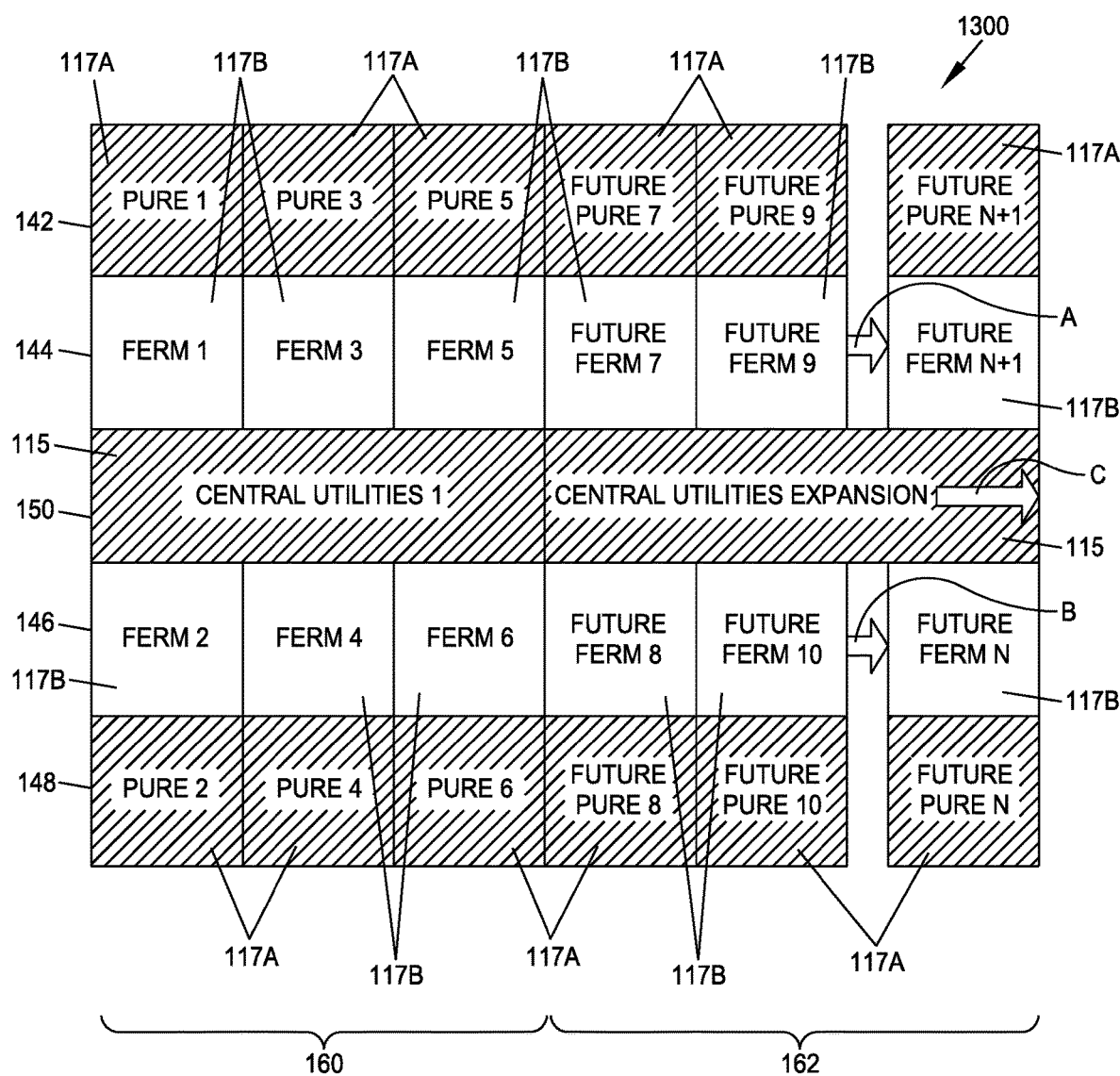
FIG. 10 is a top view of another arrangement of modular units and central units.

In some embodiments, the hub and spoke arrangement can resemble the letter H, such as in the plan view of FIG. 6. In other embodiments, the hub and spoke arrangement does not resemble the letter H. Other shapes are possible, including but not limited to: a square, a rectangle, a pentagon, and other geometric shapes, so long as it has a central unit (a central utility bay) with at least one modular unit extending from there. Additional shapes are possible, for example, as shown in FIG. 10. In some embodiments, for example, a linear "spine" shape can be used or an "E" shape can be used such that the hub and spoke arrangement resembles the letter E.

In some embodiments, the central unit 114 is not at the center of the arrangement of the central unit 114 and the modular units 116. The arrangement of the modular units 116 and the central unit 114 is preferably configured to reduce the number of modular units 116 required for a given set of manufacturing lines.

The modular units 116 can be segmented off from each other to reduce cross-contamination of product or suites.

Figure 8:
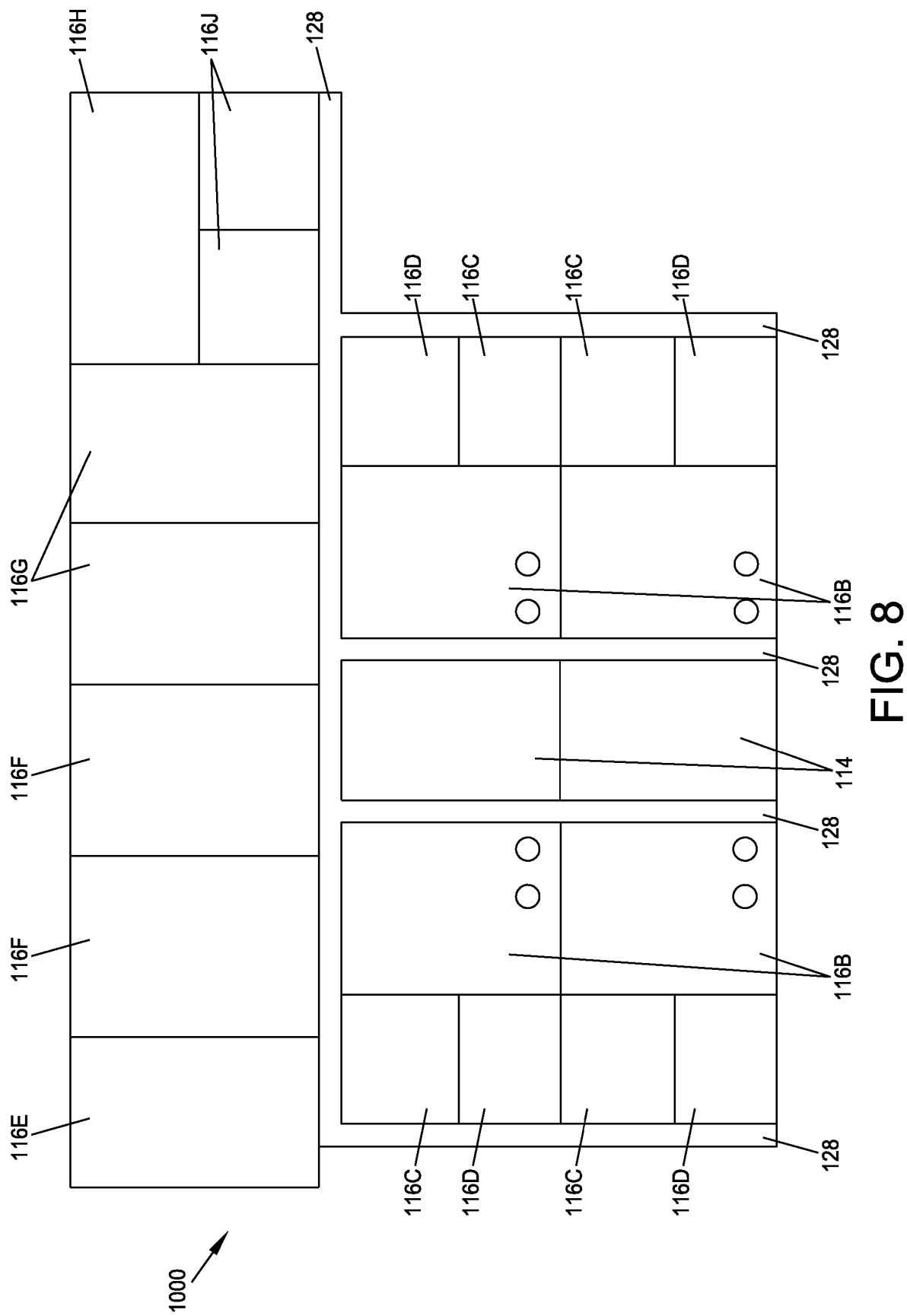
FIG. 8 is a top view of modular units and central units arranged in another arrangement within a shell.

FIG. 8 shows a plan view of another preferred embodiment of the customizable facility 1000 of the present disclosure. Two central units 114 are located towards the bottom center of the plan view of the structure shown in FIG. 8, and are positioned between shared corridors 128 that extend alongside walls of the central units 114. To the left of the central units 114 is a grouping of six modular units. This grouping includes two pre-viral units 116C, two post-viral units 116D, and two fermentation units 116B. To the right of the central units 114 as shown in FIG. 8 is a grouping of six modular units, including two pre-viral units 116C, two post-viral units 116D, and two fermentation units 116B. This configuration is designed to expand additional capability as needed (e.g., see FIG. 10 as example of an embodiment showing expansion options). Along the top of the facility 1000 as shown in FIG. 8, there are other modular units, including a utility yard unit 116E, two warehouse units 116F, two media/buffer facility units 116G, and office unit 116H, and two personnel access units 116J. Not shown in this figure is the capability to add independent buffer hold modular units directly above each purification unit. Shared corridors 128 extend along walls of the units, so that users can access each of the modular units of FIG. 8 and the central units 114 from a common corridor 128.

The different units can have different classification levels based on grading standards. For example, different units can have different classification levels based on grading standards set by the United States Food and Drug Administration or grading standards set by *EudraLex, The Rules Governing Medicinal Products in the European Union Volume* 4 *EU Guidelines to Good Manufacturing Practice Medicinal Products for Human and Veterinary Use*, supplemented by *Annex* 1 *Manufacture of Sterile Medicinal Products* in the European Union. For example, the pre-viral units 116C, the post-viral units 116D, and the media/buffer facility units 116G in FIG. 8 are classified as "Grade C," while the fermentation units 116B are classified as "Grade D," according to the European Union standards, and the remaining units are unclassified. Other classifications for the units are possible, and can be selected according to user needs.

Figure 9:
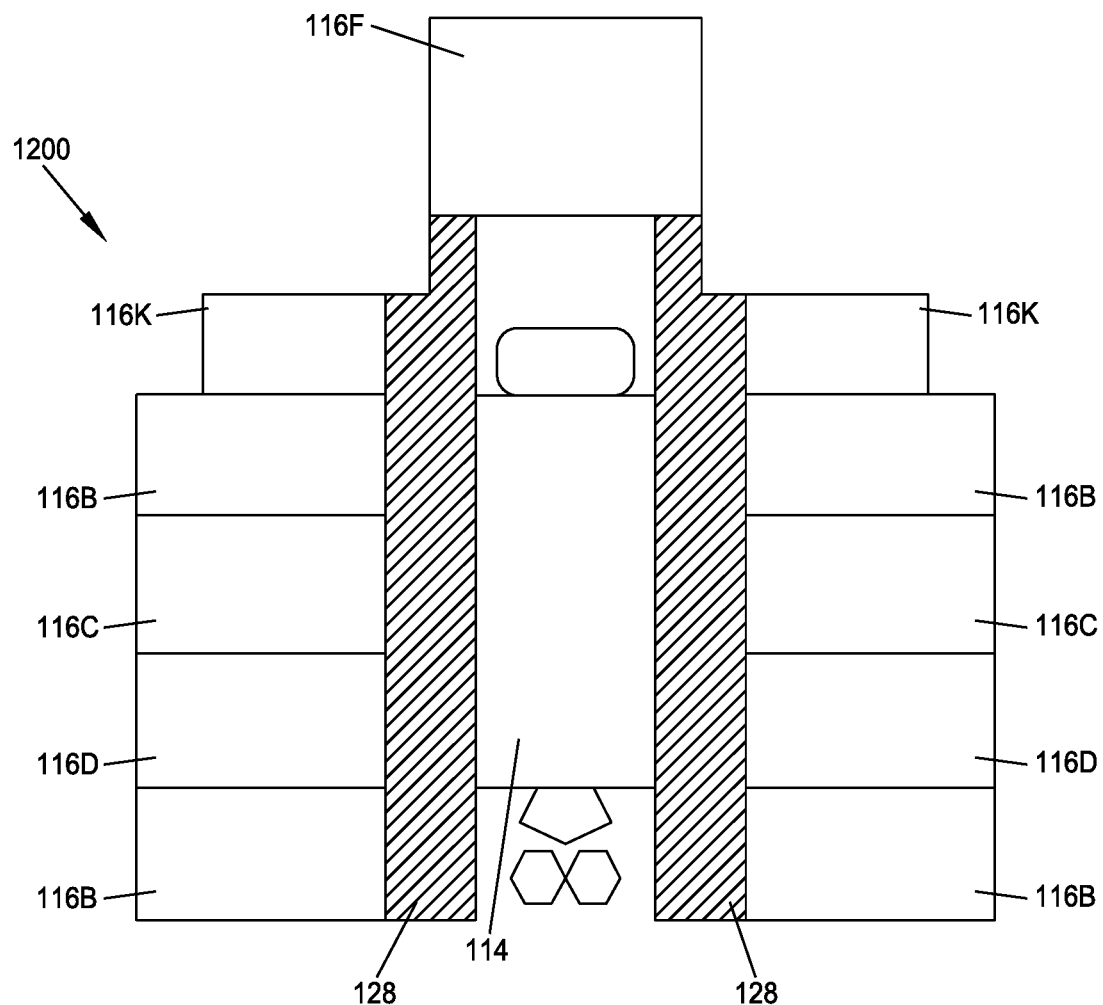
FIG. 9 is a top view of another arrangement of modular units and central units arranged within a shell.

FIG. 9 shows another embodiment of a customizable facility 1200 of the present disclosure. FIG. 9 includes a central unit (a central utilities building) 114 having corridors 128 for clean material and personnel on either side of the central unit 114. The corridors 128 extend from a warehouse 116F at an upper end of the facility 1200 shown in FIG. 9 and extend beyond the central unit 114 at the bottom of the facility. On outer sides of the respective corridors 128 are locker room units 116K, pre-viral units 116C, post-viral units 116D, and fermentation units 116B.

In an embodiment such as the one shown in FIG. 9, the fermentation units 116B each have dimensions of 63 feet by 65 feet, and are 35 feet high. In an embodiment such as the one shown in FIG. 9, the pre-viral units 116C may have dimensions of 62 feet by 50 feet, and are 17 feet high. In an embodiment such as the one shown in FIG. 9, the post-viral units 116D each have dimensions of 62 feet by 65 feet, and are 35 feet high. In other embodiments, the units may have other dimensions.

FIG. 10 shows another embodiment of a customizable facility 1300 of the present disclosure, with the shell 112 not shown. FIG. 10 includes five rows of zones. A first row (a top row) 142 in the plan view of FIG. 10 includes purification zones 117A. A second row 144 includes fermentation zones 117B. A third row 150 includes a central utilities zone 114. A fourth row 146 includes fermentation zones 117B. A fifth row 148 includes purification zones 117A.

In some aspects, a customizable facility for manufacturing at least one pharmaceutical product may include at least one central unit and at least one modular unit, but the customizable facility does not include a shell. Each modular unit is in communication with the at least one central unit such that the at least one central unit provides utilities to each modular unit.

The zones in solid lines indicate a set of zones that may be provided in an initial configuration. In this initial configuration 160, there are three purification zones (PURE 1, PURE 3, PURE 5) 117A in the first row 142, three fermentation zones (FERM 1, FERM 3, FERM 5) 117B in the second row 144, a central utilities zone (CENTRAL UTILITIES 1) 115 in the third row 150, three fermentation zones (FERM 2, FERM 4, FERM 6) 117B in the fourth row 146, and three purification zones (PURE 2, PURE 4, PURE 6) 117A in the fifth row 148.

A set of zones 162 could be added by extending an array of zones to the right. For example, two additional purification zones (PURE 7, PURE 9) 117A could be added to the first row 142, two additional fermentation zones (FERM 7, FERM 9) 117B could be added to the second row 144; additional central utilities zones 114 could be added to the third row 150, two additional fermentation zones (FERM 8, FERM 10) 117B could be added to the fourth row 146, and two additional purification zones (PURE 8, PURE 10) 117A could be added to the fifth row 148. Arrows to the right, such as the arrow A between the fermentation zones 117B labeled FERM 9 and FERM N+1, indicate the direction of potential expansion of the arrangement of zones. Additional zones could be added to the respective rows as needed, and FIG. 10 shows a purification unit (PURE N+1) 117A at the end of the first row 142, a fermentation zone (FERM N+1) 117B at the end of the second row 144, a fermentation zone (FERM N) 117B along the direction of arrow B at the end of the fourth row 146, and a purification zone (PURE N) 117A at the end of the fifth row 148. The value of N can be an integer value selected by a user as needed, and is limited only by the internal dimensions of the shell 112 within which the modular units 116 and central unit(s) 114 are positioned.

The third row can be expanded by adding central utilities zones 114 to the third row 150 along an arrow C.

The zones of FIG. 10 are regions in that could each be a central unit or a modular unit (e.g., a fermentation unit, a purification unit, etc.), or regions that could support equipment for a unit. Where FIG. 10 shows a zone (such as zone FERM 1), this zone can be subdivided into a fermentation unit FERM 1 and one or more hallways within the zone. In at least some zones, a unit can occupy the entire zone.

Modular units 116 disclosed herein may be further subdivided into sub-units. For example, a unit could have a pre-viral sub-unit and a post-viral sub-unit. The post-viral sub-unit is virus-free.

In relation to FIGS. 4-9, although the figures show views that are divided into regions that are described as units, the regions of the views can designate zones (such as a purification zone, a fermentation zone, etc.), which each include a unit and one or more hallways for connecting units.

Figure 11:
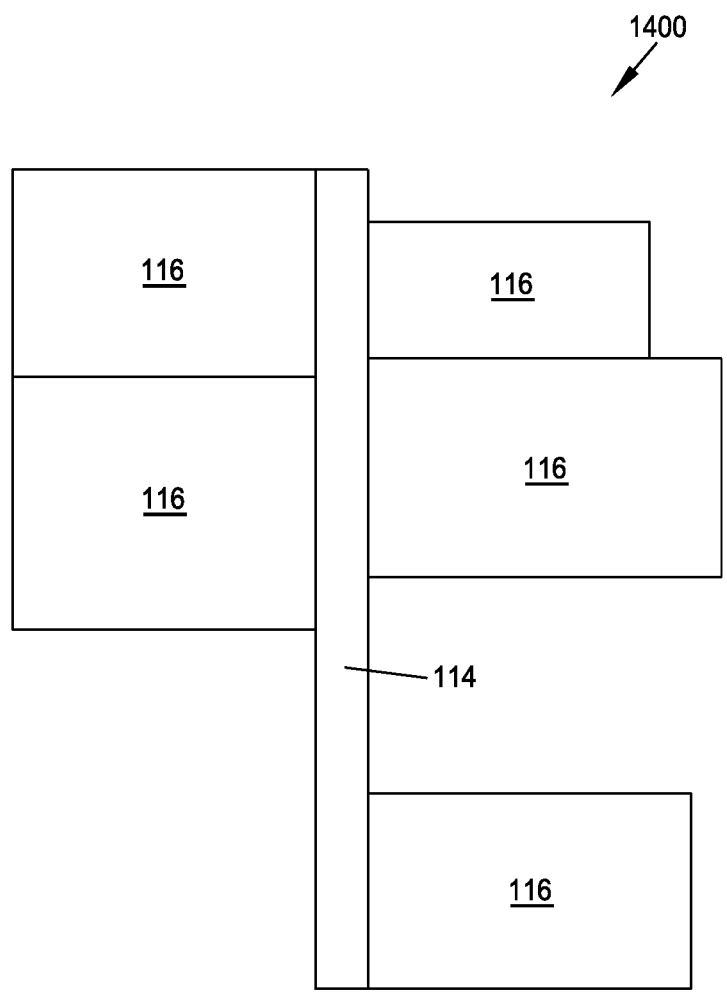
FIG. 11 is a schematic view of a set of modular units and a central unit arranged in a spine.

FIG. 11 illustrates another example embodiment of a facility 1400 in which a central unit 114 is in the shape of a linear "spine" with a plurality of modules 116 emanating from the spine. In this embodiment, the modules 116 can be added subsequently in multiple construction phases such that the facility is expanded over time.

According to an aspect of the present disclosure, a method of assembling a facility for manufacturing at least one pharmaceutical product may include providing a shell, positioning at least one central unit at least partially within the shell, and positioning at least one modular unit at least partially within the shell.

Example of a Fermentation Unit

The fermentation unit 116B houses equipment suitable for cell culture and/or fermentation. For example, equipment for cell culture and fermentation include, but are not limited to, bioreactors (e.g., suitable for culturing cells or fermentation), tanks (e.g., suitable for housing cells, media or products produced by cells), decanting apparatus, centrifuges, pumps, and other equipment useful for product recovery. Refold tanks and microfiltration units would be included for microbial fermentation processes.

In one embodiment, the fermentation unit 116B contains one or more bioreactor units suitable for culturing cells. A bioreactor unit can perform one or more, or all, of the following: feeding of nutrients and/or carbon sources, injection of suitable gas (e.g., oxygen), flow of fermentation or cell culture medium, separation of gas and liquid phases, maintenance of growth temperature, maintenance of pH level, agitation (e.g., stirring), and/or cleaning/sterilizing. The fermentation unit may contain one, 2, 3, 4, 5, 10, 15, 20, 25, 30, 35, 40, 45, 50, 60, 70, 80, 90, or 100, or more bioreactors. In various embodiments, the bioreactor is suitable for batch, semi fed-batch, fed-batch, perfusion, and/or continuous fermentation processes. In one embodiment, the bioreactor is a stirred tank reactor. In one embodiment, the bioreactor is an airlift reactor. In one embodiment, the bioreactor can have a volume between about 100 milliliters and about 50,000 liters. Non-limiting examples include a volume of 100 milliliters, 250 milliliters, 500 milliliters, 750 milliliters, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, or 50,000 liters.

In one embodiment, the bioreactor is suitable for culturing suspension cells or anchorage-dependent (adherent) cells. In one embodiment, the fermentation suite is suitable for cell therapy and/or viral therapy operations. In one embodiment, the bioreactor is suitable for culturing prokaryotic cells or eukaryotic cells. Examples of cells include, but are not limited to, bacterial cells (e.g., *E. coli. P. pastoris*), yeast cells (e.g., *S. cerevisae, T. reesei*), plant cells, insect cells (e.g., Sf9), Chinese hamster ovary cells (CHO, and any genetically modified or derived CHO cell line), mouse cells (e.g., mouse embryonic fibroblasts, cells derived from mouse cancer models), human cells (e.g., cells from any tissue or organ, cells from a cancer or other diseased cell line, stem cell), hybridoma cells, or other genetically modified or hybrid cells. In one embodiment, the cells express or produce a product, such as a recombinant therapeutic or diagnostic product. Examples of products produced by cells include, but are not limited to, antibody molecules (e.g., monoclonal antibodies, bispecific antibodies), fusion proteins (e.g., Fc fusion proteins, chimeric cytokines), other recombinant proteins (e.g., glycosylated proteins, enzymes, hormones), or lipid-encapsulated particles (e.g., exosomes, virus-like particles). In embodiments, the fermentation unit also contains equipment for separation, purification, and isolation of such products from the cells. In one embodiment, the facility and/or bioreactor can be used for producing biosimilar products.

In embodiments, the fermentation unit is in compliance with good manufacturing process and biological safety standards. In one embodiment, the fermentation unit is compliant with biosafety level 1 (BSL1), biosafety level 2 (BSL2), biosafety level 3 (BSL3), or biosafety level 4 (BSL4).

The fermentation unit can comprise sub-compartments in which each sub-compartment can be used to perform a different function or aspect that supports the cell culture, fermentation, and production processes. By way of example, the fermentation unit comprises a sub-compartment that houses one or more bioreactors, a sub-compartment that houses equipment for product recovery, a sub-compartment for inoclum, and a sub-compartment for cleaning and decontamination of equipment and the operators handling such equipment.

Example of a Down Stream Processing Unit

The purification units 116A discussed above are examples of downstream processing units.

As one example, a standard downstream processing (DSP) unit includes pre-viral separation and post-viral separation sub-units. While viral reduction does occur throughout a typical mammalian cell derived protein purification, the critical viral reduction step is considered to be the appropriate point for spatial segregation with the post-viral separation sub-unit to be considered essentially virus free. The post-viral separation sub-unit houses equipment and utilities suitable for any one of the following: ultrafiltration (tangential filtration), normal filtration, chromatography, formulation, titration, mixing, concentration, buffer exchange, bulk drug substance container filling and freezing.

The descriptions of the various embodiments and/or examples of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The descriptions of the various embodiments of the present disclosure can be utilized in the production of pharmaceuticals and biopharmaceutical products. The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 milliliters, 250 milliliters, 500 milliliters, 750 milliliters, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris*, *Pichia methanolica*, *Pichia kluyveri*, and *Pichia angusta*), *Komagataella* genus (e.g. *Komagataella pastoris*, *Komagataella pseudopastoris* or *Komagataella phaffii*), *Saccharomyces* genus (e.g. *Saccharomyces cerevisae*, *cerevisiae*, *Saccharomyces kluyveri*, *Saccharomyces uvarum*), *Kluyveromyces* genus (e.g. *Kluyveromyces lactis*, *Kluyveromyces marxianus*), the *Candida* genus (e.g. *Candida utilis*, *Candida cacaoi*, *Candida boidinii*), the *Geotrichum* genus (e.g. *Geotrichum fermentans*), *Hansenula polymorpha*, *Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger*, *A. fumigatus*, *A. orzyae*, *A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus*, *Ctenomyces*, *Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium*, *Sporotrichum* (such as *S. thermophile*), *Thielavia* (such as *T. terrestris*, *T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora*, *Bacillariophyceae*, *Dunaliella*, *Chlorella*, *Chlamydomonas*, *Cyanophyta* (cyanobacteria), *Nannochloropsis*, *Spirulina*, or *Ochromonas*), or a plant cell (e.g., cells from monocotyledonous plants (e.g., maize, rice, wheat, or

*Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West $12^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE 1

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |

TABLE 1-continued

| Protein Product | Reference Listed Drug |
|---|---|
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |

TABLE 1-continued

| Protein Product | Reference Listed Drug |
|---|---|
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |

TABLE 2-continued

Exemplary Products

| Therapeutic Product type | Product | Trade Name |
|---|---|---|
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

Unless defined otherwise, all technical and scientific terms used herein have the same meaning as commonly understood by one of ordinary skill in the art to which the disclosure pertains. Although any methods and materials similar or equivalent to those described herein can be used in the practice of and/or for the testing of the present disclosure, the preferred materials and methods are described herein. In describing and claiming the present disclosure, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a modular unit" can mean one modular unit or more than one modular unit.

Without further description, it is believed that one of ordinary skill in the art can, using the preceding description and illustrative examples, make and utilize the customizable facility of the present disclosure.

While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A customizable facility for manufacturing at least one pharmaceutical product, the customizable facility comprising:
at least one central unit positioned on a ground surface floor of the customizable facility; and
a plurality of modular units in communication with the at least one central unit such that the at least one central unit provides shared utilities to each modular unit the plurality of modular units including
a first set of modular units located at least one floor vertically above the at least one central unit for manufacturing a first pharmaceutical product, the first set of modular units having a first modular unit that is a fermentation unit, a second modular unit that is a pre-viral unit, a third modular unit that is a post-viral unit, a fourth modular unit that is a fill-finish unit, a fifth modular unit that is a dosage formulation unit, and a sixth modular unit that is a packaging unit, and a second set of modular units located at least one floor vertically above the at least one central unit for manufacturing a second pharmaceutical product, the second set of modular units having a seventh modular unit that is a fermentation unit, an eighth modular unit that is a pre-viral unit, a ninth modular unit that is a post-viral unit, a tenth modular unit that is a fill-finish unit, an eleventh modular unit that is a dosage formulation unit, and a twelfth modular unit that is a packaging unit; and a shell, wherein the at least one central unit is positioned at least partially within the shell and the plurality of modular units are positioned at least partially within the shell, and the shell is supported on footings secured in the ground surface.

2. The customizable facility of claim 1, wherein the plurality of modular units includes at least one of a utility space, a warehouse, a media buffer facility, an office, a personnel unit, and a production unit.

3. The customizable facility of claim 1, wherein the plurality of modular units is arranged to maximize a number of modular units within the shell while minimizing a footprint of the shell.

4. The customizable facility of claim 1, further comprising a bioreactor supported on the ground surface within the shell.

5. The customizable facility of claim 1, further comprising a bioreactor supported within one of the plurality of modular units.

6. The customizable facility of claim 1, wherein an outer wall of the customizable facility is one of:
 formed by the shell, the shell entirely enclosing the at least one central unit and the plurality of modular units; and
 formed by the shell and at least one of an outer wall of the at least one central unit and an outer wall of at least one modular unit of the plurality of modular units.

7. The customizable facility of claim 1, wherein the shell includes at least one side wall, the at least one side wall encircling the at least one central unit and the plurality of modular units, and a roof secured to an upper edge of the at least one side wall, the roof extending over the at least one central unit and the plurality of modular units.

8. The customizable facility of claim 1, wherein at least one of the plurality of modular units is configured for cell therapy operations.

9. A method of assembling a facility for manufacturing at least one pharmaceutical product, the method comprising:
 providing at least one central unit positioned on a ground surface floor of the customizable facility; and
 providing a plurality of modular units in communication with the at least one central unit such that the at least one central unit provides shared utilities to each modular unit, the plurality of modular units including
  a first set of modular units located at least one floor vertically above the at least one central unit for manufacturing a first pharmaceutical product, the first set of modular units having a first modular unit that is a fermentation unit, a second modular unit that is a pre-viral unit, a third modular unit that is a post-viral unit, a fourth modular unit that is a fill-finish unit, a fifth modular unit that is a dosage formulation unit, and a sixth modular unit that is a packaging unit, and a second set of modular units located at least one floor vertically above the at least one central unit for manufacturing a second pharmaceutical product, the second set of modular units having a seventh modular unit that is a fermentation unit, an eighth modular unit that is a pre-viral unit, a ninth modular unit that is a post-viral unit, a tenth modular unit that is a fill-finish unit, an eleventh modular unit that is a dosage formulation unit, and a twelfth modular unit that is a packaging unit; and
 a shell, wherein the at least one central unit is positioned at least partially within the shell and the plurality of modular units are positioned at least partially within the shell, and the shell is supported on footings secured in the ground surface.

10. The method of claim 9, wherein the plurality of modular units includes at least one of a utility space, a warehouse, a media buffer facility, an office, a personnel unit, and a production unit.

11. The method of claim 9, wherein the plurality of modular units is arranged to maximize a number of modular units within the shell while minimizing a footprint of the shell.

12. The method of claim 9, further comprising one of supporting a bioreactor on the ground surface within the shell and supporting a bioreactor within one of the plurality of modular units.

13. The method of claim 9, wherein an outer wall of the customizable facility is one of:
 formed by the shell, the shell entirely enclosing the at least one central unit and the plurality of modular units; and
 formed by the shell and at least one of an outer wall of the at least one central unit and an outer wall of at least one modular unit of the plurality of modular units.

14. The method of claim 9, wherein the shell includes at least one side wall, the at least one side wall encircling the at least one central unit and the plurality of modular units, and a roof secured to an upper edge of the at least one side wall, the roof extending over the at least one central unit and the plurality of modular units.

15. The method of claim 9, wherein the at least one pharmaceutical product is a biosimilar product.

16. The customizable facility of claim 1, wherein a number of a modular unit of the first set of modular units is increased or decreased depending on demand for the first pharmaceutical product.

17. The customizable facility of claim 1, wherein a dimension of a modular unit of the first set of modular units is increased or decreased depending on demand for the first pharmaceutical product.

18. The customizable facility of claim 1, wherein a number of a modular unit of the second set of modular units is increased or decreased depending on demand for the second pharmaceutical product.

19. The customizable facility of claim 1, wherein a dimension of a modular unit of the second set of modular units is increased or decreased depending on demand for the second pharmaceutical product.

20. The method of claim 9, further comprising increasing or decreasing a number of a modular unit of the first set of modular units depending on demand for the first pharmaceutical product.

21. The method of claim 9, further comprising increasing or decreasing a dimension of a modular unit of the first set of modular units depending on demand for the first pharmaceutical product.

22. The method of claim 9, further comprising increasing or decreasing a number of a modular unit of the second set of modular units depending on demand for the second pharmaceutical product.

23. The method of claim 9, further comprising increasing or decreasing a dimension of a modular unit of the second set of modular units depending on demand for the second pharmaceutical product.

24. The customizable facility of claim 1, wherein the first set of modular units and the second set of modular units each has a footprint that is at least 1,500 square meters.

25. The method of claim 9, wherein the first set of modular units and the second set of modular units each has a footprint that is at least 1,500 square meters.

26. The customizable facility of claim 1, wherein the first set of modular units and the second set of modular units each has a footprint between a range of 1,500 to 3,000 square meters.

27. The method of claim 9, wherein the first set of modular units and the second set of modular units each has a footprint between a range of 1,500 to 3,000 square meters.

\* \* \* \* \*